United States Patent [19]
Noe

[11] Patent Number: 5,912,395
[45] Date of Patent: Jun. 15, 1999

[54] RAFFINATE LINE FLUSH IN SIMULATED CONTINUOUS MOVING BED ADSORPTIVE SEPARATION PROCESS

[75] Inventor: Robert J.L. Noe, Mt. Prospect, Ill.

[73] Assignee: UOP LLC, Des Plaines, Ill.

[21] Appl. No.: 09/020,971

[22] Filed: Feb. 9, 1998

Related U.S. Application Data

[60] Provisional application No. 60/040,531, Mar. 12, 1997.

[51] Int. Cl.⁶ .................................................. C07C 7/12
[52] U.S. Cl. .................... 585/820; 585/821; 585/822; 585/823; 585/824; 585/826; 585/827; 585/828; 585/829
[58] Field of Search ....................... 585/820, 821, 585/822, 823, 824, 826, 827, 828, 829

[56] References Cited

U.S. PATENT DOCUMENTS

| | | | |
|---|---|---|---|
| 3,201,491 | 8/1965 | Stine et al. | 260/676 |
| 3,686,342 | 8/1972 | Neuzil | 260/674 SA |
| 4,029,717 | 6/1977 | Healy et al. | 260/674 SA |
| 4,031,156 | 6/1977 | Geissler et al. | 260/674 SA |

FOREIGN PATENT DOCUMENTS

WO 95/07740  3/1995  WIPO .

OTHER PUBLICATIONS

Broughton, D.B., R.W. Neuzil, J.M. Pharis, and C.S. Brearley, "The Parex Process for Recovering Paraxylene," *Chemical Engineering Progress* (vol. 66, No. 9) Sep. 1970, pp. 70–75.

Broughton, D.B. and S.A. Gembicki, "Adsorptive Separations by Simulated Moving Bed Technology: The Sorbex Process," presented at the International Conference on Fundamental of Adsorption, Schloss Elmau, Upper Bavaria, West Germany, May 6–11, 1983.

*Primary Examiner*—Walter D. Griffin
*Assistant Examiner*—Tam M. Nguyen
*Attorney, Agent, or Firm*—Thomas K. McBride; John F. Spears, Jr.

[57] ABSTRACT

The capacity of a simulated moving bed adsorptive separation process is increased by flushing the contents of the transfer line just previously used to remove the raffinate stream from the adsorbent chamber back into the adsorbent chamber. This step is performed immediately upstream of the point of raffinate withdrawal. Preferably the feed stream to the process is used as the flushing liquid. This flush step eliminates the passage of a quantity of the raffinate material into the adsorbent chamber when the process conduit is subsequently used to charge the feed stream to the adsorbent chamber.

11 Claims, No Drawings

RAFFINATE LINE FLUSH IN SIMULATED CONTINUOUS MOVING BED ADSORPTIVE SEPARATION PROCESS

CROSS REFERENCE TO RELATED APPLICATION

This application claims benefit of the filing date of provisional application Ser. No. 60/040,531 filed Mar. 12, 1997.

FIELD OF THE INVENTION

The subject invention relates to a process for the adsorptive separation of hydrocarbons. More specifically, the invention relates to a process for the continuous simulated countercurrent adsorptive separation of aromatic hydrocarbons. A preferred application of the process is the separation of aromatic hydrocarbons such as the separation of para-xylene from a feed mixture comprising at least two xylene isomers, including the para-isomer, using a zeolitic adsorbent and a particular desorbent.

BACKGROUND OF THE INVENTION

The polyester fabrics and articles which are in wide use today are produced from a polymer of ethylene glycol and teraphthalic acid. Teraphthalic acid is produced by the oxidation of para-xylene. Para-xylene is typically recovered from a predominantly $C_8$ aromatic hydrocarbon fraction derived from various sources such as catalytic reforming by liquid-liquid extraction and/or fractional distillation. The para-xylene is commercially separated from a para-xylene-containing feed stream, usually containing all three xylene isomers, by either crystallization or adsorptive separation or a combination of these two techniques. Adsorptive separation is the newer technique and has captured the great majority of the market share of newly constructed plants for the production of para-xylene.

Essentially all of these adsorptive separation units use a simulated countercurrent movement of the adsorbent and the xylene containing feed stream. This simulation is performed using established commercial technology wherein the adsorbent is held in place in one or more cylindrical adsorbent chambers and the positions at which the streams involved in the process enter and leave the chambers are slowly shifted along the length of the beds. Normally there are at least four streams (feed, desorbent, extract and raffinate) employed in this procedure and the location at which the feed and desorbent streams enter the chamber and the extract and raffinate streams leave the chamber are simultaneous shifted in the same direction at set intervals. Each shift in location of these transfer points delivers or removes liquid from a different bed within the chamber. This shifting could be performed using a dedicated line for each stream at the entrance to each bed. However, this will greatly increase the cost of the process and therefore the lines are reused and each line carries one of the four process streams at some point in the cycle.

RELATED ART

The general technique employed in the performance of a simulated moving bed adsorptive separation is well described in the open literature. For instance a general description directed to the recovery of para-xylene was presented at page 70 of the September 1970 edition of *Chemical Engineering Progress* (Vol. 66, No 9). A generalized description of the process with an emphasis on mathematical modeling was given at the International Conference on "Fundamentals of Adsorption", Schloss Elmau, Upper Bavaria, Germany on May 6–11, 1983 by D. B. Broughton and S. A. Gembicki. U.S. Pat. No. 4,029,717 issued to F. J. Healy et al. describes a simulated moving bed adsorptive separation process for the recovery of para-xylene from a mixture of xylene isomers. Numerous other available references describe many of the mechanical parts of a simulated moving bed system, including rotary valves for distributing various liquid flows, the internals of the adsorbent chambers and control systems.

U.S. Pat. No. 3,686,342 issued to R. W. Neuzil describes the separation of para-xylene from mixed xylenes using simulated countercurrent adsorption employing a zeolitic adsorbent and para diethylbenzene as the desorbent. This combination is a good representation of a commercial operation for this particular separation.

The art includes a recognition that the presence of residual compounds in the transfer lines can have some detrimental effects on a simulated moving bed process. U.S. Pat. No. 3,201,491 issued to L. O. Stine and D. B. Broughton and International Application WO 95/07740 both address the flushing of the line used to deliver the feed stream to the adsorbent chamber as a means to increase the purity of the recovered extract or sorbate component. This step avoids contamination of the extract stream with raffinate components of the feed remaining in this line when it is subsequently used to withdraw the extract stream from the chamber. Both references employ a desorbent rich steam to flush the contents of this line back into the adsorbent chamber.

U.S. Pat. No. 4,031,156 issued to P. R. Geissler et al. is directed to an improvement to a simulated moving bed adsorptive separation process characterized as related to flush streams used in the process. This reference, however, is directed to flushing of the interstitial void spaces between adsorbent particles in the adsorbent chamber.

SUMMARY OF THE INVENTION

The invention is an improvement to simulated moving bed adsorptive separation processes and includes the step of flushing the transfer line through which the raffinate stream was just withdrawn from the adsorbent chamber, whereby the capacity of the process is increased.

A broad embodiment of the invention may be characterized as a process for the continuous simulated moving bed adsorptive separation of a desired first compound from a feed mixture comprising at least the first compound and a second compound, which process comprises passing a feed stream comprising said feed mixture through a first conduit into an adsorbent chamber which contains a number of beds of an adsorbent which selectively retains said first compound, with the adsorbent beds being separated by transfer points for the process streams used in the process; withdrawing a raffinate stream comprising the second compound from the adsorbent at a second point through a second conduit, passing a desorbent stream into the adsorbent chamber at a third point through a third conduit, and removing an extract stream comprising the desorbent and the first compound from the adsorbent chamber at a fourth point through a fourth conduit; periodically incrementing the location of the first, second, third and fourth points along the length of the adsorbent chamber and thereby changing the conduits used to carry the feed, desorbent, extract and raffinate streams to simulate countercurrent movement of the beds of adsorbent and the feed stream; and, flushing at least a portion of the residual contents of the conduit used to remove the raffinate stream from the adsorbent chamber back into the adsorbent chamber by causing a stream of liquid to flow through the second conduit and into the bed of adsorbent at a transfer point immediately upstream of the new second point at which the raffinate stream is being withdrawn from the adsorbent chamber.

DETAILED DESCRIPTION AND PREFERRED EMBODIMENTS

In numerous processes described in the patent literature zeolitic adsorbents are used to separate various hydrocarbons and other chemical compounds such as chlorinated aromatics. The chemical compound separations which have been the specific focus of these processes include linear versus nonlinear aliphatic hydrocarbons and linear versus nonlinear olefinic hydrocarbons. Another example of hydrocarbon separation by class is the recovery of either paraffins or aromatics from a feed mixture comprising both aromatics and paraffins. The subject process can be employed in these separations or in the separation of other compounds including chiral compounds for use in pharmaceuticals and fine chemicals, oxygenates such as alcohols and ethers, carbohydrates such as sugars, and dimethyl naphthalenes. Efficiency is a more important factor in the commercial success of small units producing separated chiral compounds and other fine chemicals than for large scale units such as those producing para-xylene. The following description of the subject invention will however be presented basically in terms of the separation of various isomers of dialkyl substituted monocyclic aromatics from the other isomers, which is normally performed in large scale units.

During the adsorption step of the process a feed mixture containing a mixture of isomers, such as xylene isomers, is contacted with the adsorbent at adsorption conditions and the desired isomer is selectively adsorbed and retained by the adsorbent while the other components of the feed mixture are relatively unabsorbed. The feed mixture may contain compounds other than isomers of the desired compound. For instance, a mixed xylene feed stream may contain ethylbenzene and/or $C_9$ aromatics. When the adsorbent contains a near equilibrium loading of the more selectively adsorbed isomer, it is referred to as a "rich" adsorbent. The unabsorbed raffinate components of the feed mixture are then removed from the interstitial void spaces between the particles of adsorbent and from the surface of the adsorbent. The adsorbed isomer is then recovered from the rich adsorbent by contacting the rich adsorbent with a stream comprising a desorbent material at desorption conditions. The desorbent displaces the desired isomer to form an extract stream, which is transferred to a fractionation zone for recovery of the desired isomer from the mixture containing the desired isomer and desorbent.

Processes for the adsorptive separation of para-xylene from other xylene isomers by simulated countercurrent adsorption are both widely described and widely practiced. These processes typically include at least three or four separate steps which are performed sequentially in separate zones within a mass of adsorbent retained in one or more vertical cylindrical adsorption chambers. Each of these zones normally is formed from a plurality of beds of adsorbent, sometimes referred to as subbeds, with the number of beds per zone ranging from 2 or 3 up to 8–10. The most widely practiced commercial process units typically contain about 24 beds. All of the beds are contained in one or more vertical vessels referred to herein collectively as the adsorbent chamber. The beds are structurally separated from one another by a horizontal liquid collection/distribution grid. Each grid is connected to a transfer line defining a transfer point at which process streams enter and leave the vertical adsorption chambers.

In the first step, normally being labeled as occurring in the adsorption zone or Zone I of the chamber, the feed stream is contacted with a selective adsorbent which adsorbs the desired isomer. This removes the desired isomer from the flowing liquid. This depleted liquid and any desorbent which becomes admixed with it during passage through the adsorption zone is removed from the process as a process stream referred to as the raffinate stream.

The adsorbent in Zone I is surrounded by liquid which contains the undesired isomer(s), that is with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation.

In Zone III of the adsorbent chamber(s) the desired isomer is released from the adsorbent by exposing and flushing the adsorbent with a liquid called desorbent. The released desired isomer and accompanying desorbent are removed from the adsorbent in the form of a stream referred to herein as the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the *Kirk-Othmer Encyclopedia of Chemical Technology* at page 563.

This simulation is performed using established commercial technology wherein the adsorbent is held in place in one or more cylindrical adsorbent chambers and the positions at which the streams involved in the process enter and leave the chambers are slowly shifted along the length of the beds. The singular noun chamber is used herein to refer to one or more chambers. Normally there are at least four streams (feed, desorbent, extract and raffinate) employed in this procedure and the location at which the feed and desorbent streams enter the chamber and the extract and raffinate streams leave the chamber are simultaneous shifted in the same direction at set intervals. Each shift in location of these transfer points delivers or removes liquid from a different bed within the chamber. This shifting could be performed using a dedicated line for each stream for each bed in the chamber(s). However, this will greatly increase the cost of the process and therefore the lines are used for different streams at different times. Each line carries each of the four process streams at some point in the cycle.

It is readily apparent that when a transfer line which is being used to transport a particular stream is left idle at the end of a step it will remain full of the compounds forming that stream until these compounds are removed from the line by a second flowing stream. The residual compounds left in the now unused transfer line will therefore be either withdrawn from the process as the initial part of a process stream removed from the process or forced into the adsorbent chamber when the transfer line carries a stream removed from or passed into the adsorbent chamber. As described above, those working in this art have recognized that the presence of these residual compounds in the transfer lines can have some detrimental effects on the performance of a simulated moving bed adsorptive separation process.

It is an objective of the subject invention to provide an improved process for the simulated moving bed adsorptive separation of chemical compounds. It is a further objective to provide an improved process for the adsorptive separation of aromatic hydrocarbons. It is another objective of the subject invention to provide a process which increases the capacity of a simulated moving bed adsorptive separation process to recover a selectively adsorbed compound. It is a specific objective to increase the capacity of a simulated moving bed unit to recover para-xylene from a feed stream comprising a mixture of xylene isomers.

It has been found that these objectives can be achieved by flushing the contents of the transfer line which has just been used to remove the raffinate stream from the adsorbent chamber back into the chamber using a stream of the feed material. The use of the subject invention can provide a 3 to 6 volume percent increase in the capacity of an existing unit to produce a desired adsorbed isomer. The amount of increase will depend on such factors as the amount of capacity which is lost when the raffinate components of the process are forced back into the adsorbent chamber, which will vary depending on the compounds which are being separated using this process.

It must be recognized that the subject invention is directed to flushing a transfer line which carries liquid to and from the adsorbent chamber. It is therefore not related to technology which involves flushing the beds of adsorbent material.

At least two points distinguish the subject process from the two patent documents cited above which teach flushing of the line which has just carried the feed stream into the process. First, the subject process is concerned with the flushing of a different line in the process. Whereas these documents teach flushing the line which has just been used to add the feed stream to the adsorbent chamber, the subject process flushes a different line, the one just used to remove the raffinate stream. Second, the invention flushes this line using a different media. Furthermore both the purpose and effect of the flushing steps are different. The cited documents teach that it is undesirable to leave the residue of the feed stream in the line which is subsequently used to withdraw the product stream as the raffinate components of the feed stream will contaminate the product. In contrast the subject process removes raffinate from the process line prior to the transfer line being used to pass the feed stream into the process to avoid passing the desorbent present in the raffinate stream back into the adsorbent chamber.

The passage of desorbent into the adsorbent chamber through the feed line is undesirable as the desorbent competes with the desired isomer for adsorptive sites on the adsorbent. The two compounds compete for the adsorptive capacity. A simplified summary of this is that the adsorption capacity of the adsorbent in adsorption zone (Zone I) is the sum of the desired isomer and the desorbent compound which is adsorbed on the adsorbent. Decreasing the amount of desorbent charged to the adsorption zone therefore increases the amount of adsorbent capacity available for para-xylene or any other desired compound.

Another feature which distinguishes the subject process from that of the cited documents is the location at which the contents of the line being flushed is passed into the adsorbent chamber. In the previously cited process of Stine et al., the contents of the line which has just transported the feed stream are pushed into the adsorbent chamber at a point immediately upstream of the feed inlet point. In comparison in the subject process the content of the line being flushed is passed back into the adsorbent chamber at a point just upstream of the point at which the raffinate stream was removed from the process.

The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber. This is primarily important in describing the transfer line which is flushed in the subject invention. It is the line which was used to remove the raffinate stream before the last incrementing of the transfer points during the simulation of countercurrent moving bed operation. Therefore it is the transfer line just upstream of the line presently used as the raffinate line.

The precise amount of material which is used to flush the raffinate line is not important, but measurement of this quantity is required. It is believed there is only minimal back-mixing of liquids in the transfer lines and that therefore the amount of flush liquid need not greatly exceed the total volume of the transfer line(s) which is to be flushed. The transfer "line" may be in several parts linked together by valves or some other connecting device. A broad range of the required quantity of the flush liquid is from about 0.4 to about 2.5 times this total volume. A preferred quantity of the feed stream used to flush the raffinate line and any associated valving is from 0.5 to about 1.5 times this total volume. While larger amounts of flush may at first appearance seem beneficial as they would increase the degree of raffinate removal, it must be recognized that this flush material is passed into the adsorbent chamber. Passing significant quantities of the feed stream into the chamber near the raffinate withdrawal point will change the concentration profiles in the adsorbent chamber. This may increase the quantity of the desired product that is contained in the raffinate stream.

Countercurrent simulated moving bed systems are described in many available references, such as U.S. Pat. No. 2,985,589, incorporated herein by reference for its teaching of the practice of simulated moving bed adsorptive separation processes. Cyclic advancement of the input and output streams of this simulation can be accomplished by a manifolding system or by rotary disc valves as shown in U.S. Pat. Nos. 3,040,777 and 3,422,848. Equipment utilizing these principles can vary in size from the pilot plant scale shown in U.S. Pat. No. 3,706,812 to commercial petrochemical plant scale, with flow rates ranging from a few cc per hour to many thousands of gallons per hour. Large scale plants normally employ rotary valves having a port for each transfer line while small scale and high pressure units tend to use valves having only two or three ports. The invention will normally be employed in an adsorptive separation process which simulates countercurrent movement of the adsorbent and surrounding liquid but it may also be practiced in a cocurrent continuous process, like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals.

The practice of the subject invention requires no significant changes in operating conditions, adsorbent or desorbent composition or mechanical changes in the adsorbent chambers. No new input streams are needed and the output streams are also essentially unchanged except for the resulting improvement and some minor change in composition.

The only significant required change to the process equipment is that needed to deliver a controlled quantity of the feed stream to the line to be flushed. These changes are preferably made in and near the equipment used to control the flow of the process streams to and from the adsorbent chamber essentially in the same manner as in the previously referred to Stine et al. reference. That is, the subject process may be implemented on an existing unit by a modification in the equipment which directs fluid flow. The amount of the flush material is preferably controlled by a single valve on a single line through which the flush material flows before entering the line and valve system to be flushed.

The practice of the subject invention is not believed related to or limited to the use of any particular adsorbent or adsorbent/desorbent combination. The only limitation is the effectiveness of the adsorbent/desorbent combination in the desired separation. Examples of adsorbents which may be used in the process of this invention include nonzeolitic molecular sieves including carbon-based molecular sieves, silicalite and the crystalline aluminosilicates molecular sieves classified as X and Y zeolites. The adsorbent may or may not be a zeolite. The sorptive properties of one non-zeolitic molecular sieve, ALPO-5, are described in a paper printed in the *Journal of Catalysis* 111, 23–40 (1988). Details on the composition and synthesis of many of these microporous molecular sieves are provided in U.S. Pat. No. 4,793,984, which is incorporated herein for this teaching. Information on adsorbents may also be obtained from U.S. Pat. Nos. 4,385,994; 4,605,492; 4,310,440; and, 4,440,871. Differing sieve/desorbent combinations are used for different separations. For instance, X zeolites, specifically X zeolites exchanged with barium or barium and potassium ions at their exchangeable sites, are the preferred adsorbents for p-xylene recovery from xylene mixtures.

Zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as molecular sieves when the separation which they effect is dependent essentially upon differences between the sizes of the feed molecules as, for instance, when smaller normal paraffin molecules are separated from larger isoparaffin molecules. In the preferred embodiments of this invention, however, this basis for the term molecular sieves is not strictly accurate since the separation of specific aromatic isomers is apparently also highly dependent on differences in electrochemical attraction between the different isomers and the adsorbent rather than purely on physical size differences in the isomer molecules.

In a hydrated form, the type X aluminosilicate zeolites are represented by the formula below in terms of moles of oxides:

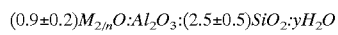

$$(0.9\pm0.2)M_{2/n}O:Al_2O_3:(2.5\pm0.5)SiO_2:yH_2O$$

where "M" is a cation having a valence of not more than 3 which balances the electrovalence of the tetrahedra and is generally referred to as an exchangeable cationic site, "n" represents the valence of the cation, and "y", which represents the moles of water, is a value up to about 9 depending upon the identity of "M" and the degree of hydration of the crystal. As noted from Formula 1, the $SiO_2/Al_2O_3$ mole ratio is 2.5±0.5. The cation "M" may be monovalent, divalent or trivalent cations or mixtures thereof. For instance, for the separation of xylenes "M" may be barium or a mixture of barium and potassium.

Zeolites are used in adsorption separations in the form of particle agglomerates having high physical strength and attrition resistance. The agglomerates used in separative processes contain the crystalline material dispersed in an amorphous, inorganic matrix or binder, having channels and cavities therein which enable liquid access to the crystalline material. Methods for forming the crystalline powders into such agglomerates include the addition of an inorganic binder, generally a clay comprising a silicon dioxide and aluminum oxide, to the high purity zeolite powder in wet mixture. The binder aids in forming or agglomerating the crystalline particles which otherwise would comprise a fine powder. The blended clay-zeolite mixture is extruded into cylindrical pellets or formed into beads which are subsequently calcined in order to convert the clay to an amorphous binder of considerable mechanical strength. The adsorbent particles may thus be in the form of extrudates, tablets, macrospheres or granules having a desired particle range, preferably from about 16 to about 60 mesh (Standard U.S. Mesh) (1.9 mm to 250 microns). Clays of the kaolin type, water permeable organic polymers or silica are generally used as binders.

Those skilled in the art will appreciate that the performance of an adsorbent is greatly influenced by a number of factors not related to its composition such as operating conditions, feed stream composition, water content of the adsorbent and the desorbent composition. The optimum adsorbent composition is therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For p-xylene recovery it is preferred that the water content of the adsorbent results in an LOI at 500° C. of less than 7.0% and preferably within the range of from 0 to 6.5 wt %.

The zeolite will ordinarily be in the form of small crystals present in the particles in amounts ranging from about 75 to about 98 wt. % of the particle based on volatile-free composition. Volatile-free compositions are generally determined after the adsorbent has been calcined at 900° C. in order to drive off all volatile matter. The remainder of the adsorbent will generally be the inorganic matrix present in intimate mixture with the small particles of the zeolite material. This matrix material may be an adjunct of the manufacturing process for the zeolite (for example, from the intentionally incomplete purification of the zeolite during its manufacture) or it may be added to relatively pure zeolite, but in either case its usual purpose is as a binder to aid in forming or agglomerating the zeolite into the hard particles.

In the practice of the present invention, a feed mixture comprising two or more isomers is passed through one or more beds of an adsorbent which selectively adsorbs the desired xylene while permitting other isomers and other components of the feed stream to pass through the adsorption zone in an unchanged condition. The flow of the feed is stopped and the adsorption zone is then flushed to remove nonadsorbed materials surrounding the adsorbent. Thereafter the desired isomer is desorbed from the adsorbent by passing a desorbent stream through the adsorbent bed. The desorbent material is commonly also used to flush nonadsorbed materials from the void spaces around and within the adsorbent.

Benzene, toluene, and p-diethylbenzene are normally described as suitable desorbents for para-xylene recovery in the references, with p-diethylbenzene (p-DEB) having become a commercial standard for the separation. P-DEB is a "heavy" desorbent (higher boiling than p-xylene) which allows for easier recovery of the desorbent from the extract and raffinate streams by fractional distillation.

For purposes of this invention, various terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

At least portions of the extract stream and the raffinate stream are passed to separation means, typically fractional distillation columns, where at least a portion of desorbent material is recovered to produce an extract product and a raffinate product. The terms "extract product" and "raffinate product" mean products produced by the process containing, respectively, an extract component and a raffinate component in higher concentrations than those found in the extract stream and the raffinate stream. The term "rich" is intended to indicate a concentration of the indicated compound or class of compounds greater than 50 mole percent.

The selectivity, ($\beta$), as used throughout this specification is defined as the ratio of the two components in the adsorbed phase divided by the ratio of the same two components in the unabsorbed phase at equilibrium conditions. Relative selectivity is given by the equation:

$$\text{Selectivity} = \frac{\text{wt. percent } C/\text{wt. percent } D_A}{\text{wt. percent } C/\text{wt. percent } D_U}$$

where C and D are two components of the feed represented in weight percent and the subscripts A and U represent the adsorbed and unabsorbed phases, respectively. The equilibrium conditions are determined when the feed passing over a bed of adsorbent does not change composition, in other words, when there is no net transfer of material occurring between the unabsorbed and adsorbed phases. Relative selectivity can be expressed not only for one feed compound as compared to another but can also be expressed between any feed mixture component and the desorbent material.

Where selectivity of two components approaches 1.0, there is no preferential adsorption of one component by the adsorbent with respect to the other; they are both adsorbed to about the same degree with respect to each other. As $\beta$ becomes less than or greater than 1.0, there is a preferential adsorption by the adsorbent for one component with respect to the other. When comparing the selectivity of the adsorbent for component C over component D, a $\beta$ larger than 1.0 indicates preferential adsorption of component C within the adsorbent. A $\beta$ less than 1.0 would indicate that component D is preferentially adsorbed leaving an unabsorbed phase richer in component C and an adsorbed phase richer in component D.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

Feed mixtures which can be utilized in the process of this invention are typically prepared by fractional distillation. They may comprise para-xylene and at least one other $C_8$ aromatic isomer, and may also contain other hydrocarbons. Thus, the feed mixtures to the process of this invention can contain sizable quantities of $C_6$, $C_7$, and $C_9$ aromatics and may also contain quantities of straight or branched chain paraffins, cycloparaffins, or olefinic material having boiling points relatively close to the desired xylene isomer. The desired xylene may be the para, meta or ortho isomer. The feed can alternatively contain a mixture of isomers of other aromatic or paraffinic hydrocarbons. Some specific examples are cresol isomers, cymene isomers and dimethyl naphthalene isomers. The subject process may also be employed to separate classes of compounds such as olefins from paraffins or straight chain paraffins from nonstraight chain; e.g., iso and cycloparaffins.

Mixtures containing substantial quantities of para-xylene, other $C_8$ aromatic isomers, and other hydrocarbons and $C_9$ aromatics generally are produced by catalytic naphtha reforming and/aromatic hydrocarbon isomerization processes. These processes are well known in the refining and petrochemical arts. In a catalytic naphtha reforming process a naphtha boiling range feed is contacted with a platinum and halogen-containing catalyst at severities selected to produce an effluent containing $C_8$ aromatic isomers. Generally, the reformate is then fractionated to concentrate the $C_8$ aromatic isomers into a $C_8$ fraction which will also contain coboiling nonaromatics and some C7 and $C_9$ aromatics. Feed mixtures for the process of this invention may also be obtained from isomerization and transalkylation processes. For instance, the transalkylation of mixtures of $C_7$ and/or $C_9$ aromatics produces xylene isomers. Xylene mixtures recovered from the adsorption zone which are deficient in one or more isomers can be isomerized, at isomerization conditions, to produce an effluent containing $C_8$ aromatic isomers, which can then be recycled to the adsorbtion zone for separation.

Adsorption conditions in general include a temperature range of from about 20° to about 250° C., with from about 60° to about 200° C. being more preferred for para-xylene separation. Adsorption conditions also include a pressure sufficient to maintain liquid phase, which may be from about atmospheric to 600 psig. Desorption conditions generally include the same range of temperatures and pressure as used for adsorption conditions. Different conditions may be preferred for other extract compounds.

One embodiment of the subject process may be characterized as a process for the continuous simulated moving bed adsorptive separation of a desired first compound from a feed mixture comprising at least the first compound and a second compound which process comprises passing a feed stream comprising said feed mixture through a first transfer line into an adsorbent chamber(s) which contains at least ten separated beds of a particulate zeolitic adsorbent which selectively retains said first compound, withdrawing a raffinate stream comprising the second compound from the adsorbent chamber at a second point through a second transfer line, passing a desorbent stream into the adsorbent chamber at a third point through a third transfer line, and removing an extract stream comprising the desorbent and the first compound from the adsorbent chamber at a fourth point through a fourth transfer line; periodically incrementing the location of the first, second, third and fourth points and thereby changing the identity of the transfer lines used to carry the feed, desorbent, extract and raffinate streams and maintaining a fluid flow through the chamber to simulate countercurrent movement of the beds of adsorbent and the feed stream through the use of a rotary valve; and, flushing at least a portion of the residual contents of the transfer line which has just been used to remove the raffinate stream from the adsorbent chamber back into the adsorbent chamber by passing a stream of liquid through this transfer line and into the adsorbent chamber.

In order to verify the improvement expected from the invention, a comparison was performed using a computerized model which has been shown to accurately predict and correlate with the actual operation of commercial scale simulated moving bed adsorptive separation units used to recover para-xylene from a mixture of xylene isomers. The simulated unit had twenty-four beds of adsorbent divided between two columns and a twenty-four port rotary valve to direct the flow of the process streams. The feed to the column was set to contain the compounds set out in Table 1. The model produced the different required adsorbent to feed ratios needed for the unit to produce an extract having the required para-xylene purity. These ratios were 0.705 without the line flush and 0.674 with the line flush. These ratios translate into an approximately 4 volume percent increase in capacity of a unit of fixed size.

TABLE 1

| Feed Composition in wt. % | |
|---|---|
| Nonaromatics | 0.68 |
| Benzene | 0.00 |
| Toluene | 0.39 |
| Ethylbenzene | 8.10 |
| P-xylene | 23.67 |
| M-xylene | 50.49 |
| O-xylene | 16.67 |
| $C_9$'s | 0.00 |
| $C_{10}$-plus | 0.00 |

What is claimed is:

1. In a process for the separation of a desired compound from a feed mixture comprising two or more chemical compounds by simulated countercurrent adsorptive separation wherein a feed stream and a desorbent stream are passed into at least one multi-bed adsorbent chamber at two different points via different transfer lines and a raffinate stream and an extract stream are individually removed from the adsorbent chamber at two different points by two additional transfer lines, the improvement which comprises using a quantity of the feed stream to flush the contents of the transfer line which has just been used to remove the raffinate stream back into the adsorbent chamber at the next upstream point from the transfer line just used to remove the raffinate stream.

2. The process of claim 1 wherein the volume of the feed stream used to flush the raffinate transfer line is equal to about 0.5 to about 2.5 times the total volume of the raffinate transfer line and associated valving.

3. A process for the continuous simulated moving bed adsorptive separation of a desired first compound from a feed mixture comprising at least the first compound and a second compound, which process comprises:

a.) passing a feed stream comprising said feed mixture through a first transfer line into an adsorbent chamber which contains a number of beds of an adsorbent which selectively retains said first compound, with the beds being separated by transfer points for streams used in the process;

b.) withdrawing a raffinate stream comprising the second compound from the adsorbent chamber at a second point through a second transfer line, passing a desorbent stream into the adsorbent chamber at a third point through a third transfer line, and removing an extract stream comprising the desorbent and the first compound from the adsorbent chamber at a fourth point through a fourth transfer line;

c.) periodically incrementing the location of the first, second, third and fourth points and thereby changing the transfer lines used to carry the feed, desorbent, extract and raffinate streams to simulate countercurrent movement of the beds of adsorbent and the feed stream; and, d.) flushing at least a portion of the residual contents of the transfer line just used to remove the raffinate stream from the adsorbent chamber back into the adsorbent chamber by causing a stream of liquid to flow through the said transfer line and into the adsorbent chamber.

4. The process of claim 3 wherein said feed mixture comprises $C_8$ aromatic hydrocarbons.

5. The process of claim 4 wherein the feed mixture comprise xylenes.

6. The process of claim 4 wherein the feed stream comprises a mixture of paraffins and aromatics.

7. The process of claim 3 wherein the feed stream comprises a mixture of normal and non-normal paraffins.

8. The process of claim 3 wherein the feed stream comprises a mixture of chiral isomers which are to be separated.

9. The process of claim 3 wherein the mixture comprises cymene isomers.

10. The process of claim 3 wherein the feed mixture comprises a mixture of dimethyl naphthalene isomers.

11. The process of claim 3 further characterized in that the material flush from the transfer line which had just previously carried the raffinate stream is passed into a bed of adsorbent at a transfer point immediately upstream of the point at which the raffinate stream is being withdrawn from the adsorbent chamber.

* * * * *